United States Patent [19]

Jelich et al.

[11] Patent Number: 5,013,351
[45] Date of Patent: May 7, 1991

[54] TRIAZOLO-PYRIMIDINE-2-SULPHONA-MIDES USEFUL AS HERBICIDES

[75] Inventors: Klaus Jelich, Wuppertal; Wolfgang Krämer, Burscheid; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 335,002

[22] Filed: Apr. 7, 1989

Related U.S. Application Data

[63] Continuation-in-part of Ser. No. 117,257, Nov. 5, 1987, abandoned.

[30] Foreign Application Priority Data

Nov. 25, 1986 [DE] Fed. Rep. of Germany ....... 3640155

[51] Int. Cl.$^5$ .................. C07D 487/04; A61K 31/14
[52] U.S. Cl. .......................................... 71/92; 544/263
[58] Field of Search ............................ 544/263; 71/92

[56] References Cited

U.S. PATENT DOCUMENTS

| | | | |
|---|---|---|---|
| 4,684,395 | 8/1987 | Levitt | 71/92 |
| 4,687,507 | 8/1987 | Levitt | 71/92 |
| 4,740,233 | 4/1988 | Kleschik et al. | 71/92 |
| 4,854,964 | 8/1989 | Jelich et al. | 544/253 |

Primary Examiner—Mukund J. Shah
Assistant Examiner—Jyothsna Venkat
Attorney, Agent, or Firm—Sprung Horn Kramer & Woods

[57] ABSTRACT

Novel herbicides of the formula

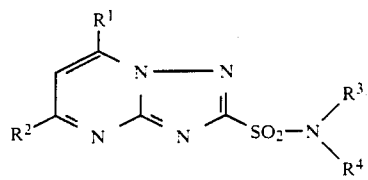

in which
$R^1$ represents —$CH_2$—O—$R^5$ and at the same time $R^2$ represents alkyl, or
$R^2$ represents —$CH_2$—O—$R^5$ and at the same time $R^1$ represents alkyl,
$R^3$ represents hydrogen, alkyl, alkylcarbonyl, alkoxycarbonyl, alkylsulphonyl, alkenyl or alkinyl, or represents optionally substituted aralkyl,
$R^4$ represents aryl or heteroaryl, in each case optionally substituted, and
$R^5$ represents alkyl.

10 Claims, No Drawings

TRIAZOLO-PYRIMIDINE-2-SULPHONAMIDES USEFUL AS HERBICIDES

CROSS REFERENCE TO RELATED APPLICATION

This application is a continuation-in-part application of application Ser. No. 07/117,257, filed Nov. 5, 1987, now abandoned.

The invention relates to new triazolo-pyrimidine-2-sulphonamides, several processes and new intermediate products for their preparation and their use as herbicides.

It is already known that certain triazolo-pyrimidine-2-sulphonamide derivatives, such as, for example, 2,6-dimethyl-N-(2-methoxycarbonylphenyl)-1,2,4-triazolo-[1,5-a]-pyrimidine-2-sulphonamide, have herbicidal properties (See, for example, European Patent A-142,152).

However, the herbicidal activity of these already known compounds towards certain problem weeds, like their tolerance by certain crop plants, is not always completely satisfactory.

New triazolo-pyrimidine-2-sulphonamides of the general formula (I)

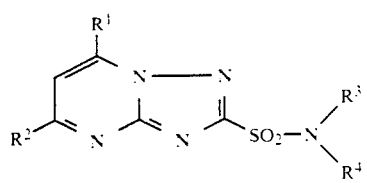

in which
R$^1$ represents a radical —CH$_2$—O—R$^5$ and at the same time R$^2$ represents alkyl, or
R$^2$ represents a radical —CH$_2$—O—R$^5$ and at the same time R$^1$ represents alkyl,
R$^3$ represents hydrogen, alkyl, alkylcarbonyl, alkoxycarbonyl, alkylsulphonyl, alkenyl or alkinyl, or represents optionally substituted aralkyl,
R$^4$ represents aryl or heteroaryl, in each case optionally substituted, and
R$^5$ represents alkyl, have been found.

It has furthermore been found that the new triazolo-pyrimidine-2-sulphonamides of the general formula (I)

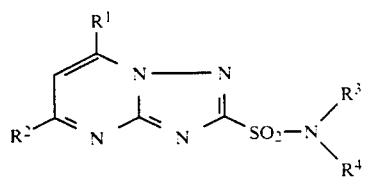

in which
R$^1$ represents a radical —CH$_2$—O—R$^5$ and at the same time R$^2$ represents alkyl, or
R$^2$ represents a radical —CH$_2$—O—R$^5$ and at the same time R$^1$ represents alkyl,
R$^3$ represents hydrogen, alkyl, alkylcarbonyl, alkoxycarbonyl, alkylsulphonyl, alkenyl or alkinyl, or represents optionally substituted aralkyl,
R$^4$ represents aryl or heteroaryl, in each case optionally substituted, and
R$^5$ represents alkyl, are obtained by one of the processes described below:
(a) triazolo-pyrimidine-2-sulphonamides of the formula (Ia)

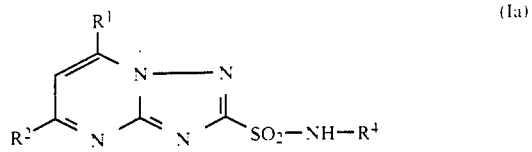

in which
R$^1$, R$^2$ and R$^4$ have the abovementioned meaning, are obtained by a process in which amino-triazolylsulphonamides of the formula (II)

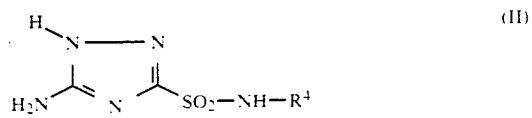

in which
R$^4$ has the abovementioned meaning, are reacted with 1,3-diketones of the formula (III)

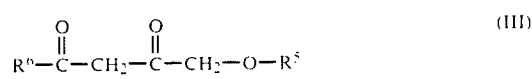

in which
R$^5$ has the abovementioned meaning and
R$^6$ represents alkyl,
if appropriate in the presence of a diluent; or (b) triazolo-pyrimidine-2-sulphonamides of the formula (Ib)

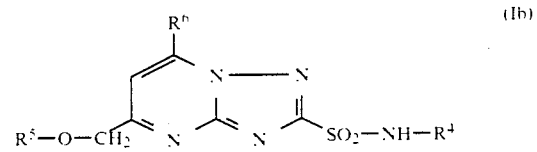

in which
R$^4$ and R$^5$ have the abovementioned meaning and
R$^6$ represents alkyl,
are obtained by a process in which triazolo-pyrimidine-2-sulphonyl chlorides of the formula (IV)

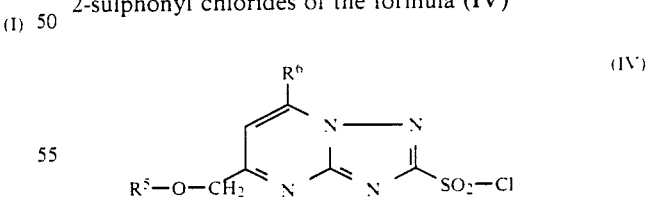

R$^5$ and R$^6$ have the abovementioned meaning, are reacted with amines of the formula (V)

in which
R$^4$ has the abovementioned meaning, if appropriate in the presence of a diluent and if appropriate in the presence of an acid-binding agent; or (c) triazolo-pyrimidine-2-sulphonamides of the formula (Ic)

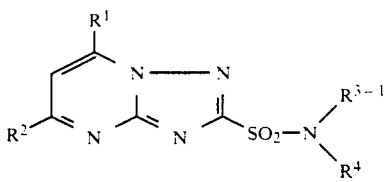

(Ic)

in which $R^1$, $R^2$ and $R^4$ have the abovementioned meaning and $R^{3-1}$ represents alkyl, alkenyl or alkinyl, or represents optionally substituted aralkyl, or represents alkylcarbonyl, alkoxycarbonyl or alkylsulphonyl, are obtained by a process in which the triazolo-pyrimidine-2-sulphonamides obtainable by process (a) or (b), of the formula (Ia)

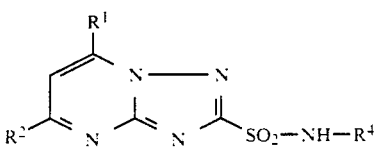

(Ia)

in which $R^1$, $R^2$ and $R^4$ have the abovementioned meaning, are reacted with alkylating, acylating or sulphonylating agents of the formula (VI)

 (VI)

in which $R^{3-1}$ has the abovementioned meaning and Y represents an electron-withdrawing leaving group, if appropriate in the presence of a diluent and if appropriate in the presence of a base.

Finally, it has been found that the new triazolopyrimidine-2-sulphonamides of the general formula (I) have herbicidal properties.

Surprisingly, the triazolo-pyrimidine-2-sulphonamides of the general formula (I) exhibit a considerably better herbicidal activity against problem weeds than the triazolo-pyrimidine-2-sulphonamide derivatives known from the prior art, such as, for example, 2,6-dimethyl-N-(2-methoxycarbonylphenyl)-1,2,4-triazolo-[1,5-a]-pyrimidine-2-sulphonamide, these being closely related compounds, both chemically and from the point of view of their action.

Formula (I) provides a general definition of the triazolo-pyrimidine-2-sulphonamides according to the invention. Preferred compounds of the formula (I) are those in which $R^1$ represents a radical $—CH_2—O—R^5$, and at the same time $R^2$ represents straight-chain or branched alkyl with 1 to 6 carbon atoms, or $R^2$ represents a radical $—CH_2—O—R^5$, and at the same time $R^1$ represents straight-chain or branched alkyl with 1 to 6 carbon atoms, wherein $R^5$ in both cases in each case represents straight-chain or branched alkyl with 1 to 6 carbon atoms, $R^3$ represents hydrogen, or represents in each case straight-chain or branched alkyl, alkylcarbonyl, alkoxycarbonyl or alkylsulphonyl with in each case 1 to 4 carbon atoms in the individual alkyl parts, or represents in each case straight-chain or branched alkenyl or alkinyl with in each case 3 to 6 carbon atoms, or represents aralkyl which has 1 to 4 carbon atoms in the alkyl part and 6 to 10 carbon atoms in the aryl part and is straight-chain or branched in the alkyl part and optionally monosubstituted or polysubstituted by identical or different substituents in the aryl part, possible substituents on the aryl being: fluorine, chlorine, bromine, iodine, cyano, nitro, hydroxyl and in each case straight-chain or branched alkyl, alkoxy, alkylthio, halogenoalkyl, halogenoalkoxy and halogenoalkylthio with in each case 1 to 4 carbon atoms and if appropriate 1 to 9 identical or different halogen atoms, and $R^4$ represents aryl which has 6 to 10 carbon atoms and is optionally monosubstituted or polysubstituted by identical or different substituents, or represents a 5- to 7-membered heterocyclic radical which has 1 to 3 hetero atoms, in particular nitrogen, oxygen and/or sulphur, and is optionally monosubstituted or polysubstituted by identical or different substituents and/or benzo-fused, possible substituents in each case being: fluorine, chlorine, bromine, iodine, cyano, nitro, hydroxyl, in each case straight-chain or branched alkyl, alkoxy, alkylthio, alkylcarbonyl, alkylsulphinyl and alkylsulphonyl with in each case 1 to 6 carbon atoms, in each case straight-chain or branched halogenoalkyl, halogenoalkoxy, halogenoalkylthio, halogenoalkylsulphinyl, halogenoalkylsulphonyl, halogenoalkylcarbonyl or halogenoalkoxycarbonyl with in each case 1 to 6 carbon atoms and 1 to 9 identical or different halogen atoms, phenyl, phenoxy, phenylthio, phenylcarbonyl, hydroxycarbonyl, in each case straight-chain or branched alkoxycarbonyl, alkenyloxycarbonyl and alkoxyalkoxycarbonyl with in each case 1 to 6 carbon atoms in the individual alkyl parts and 3 to 6 carbon atoms in the alkenyl part, and hydroximinoalkyl and straight-chain or branched alkoximinoalkyl with in each case 1 to 4 carbon atoms in the individual alkyl parts.

Particularly preferred compounds of the general formula (I) are those in which $R^1$ represents a radical $—CH_2—O—CH_3$ or $—CH_2—O—C_2H_5$, and at the same time $R^2$ represents methyl or ethyl, or $R^2$ represents a radical $—CH_2—O—CH_3$ or $—CH_2—O—C_2H_5$, and at the same time $R^1$ represents methyl or ethyl, $R^3$ represents hydrogen, methyl, ethyl, acetyl, methoxycarbonyl, ethoxycarbonyl, methylsulphonyl, allyl, propargyl or benzyl and $R^4$ represents phenyl or naphthyl, in each case optionally mono-, di- or trisubstituted by identical or different substituents, or represents a heterocyclic radical of the formula

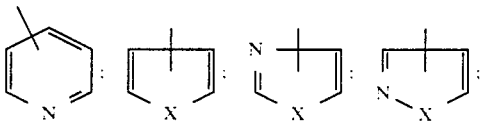

which is optionally mono-, di- or trisubstituted by identical or different substituents and/or benzo-fused, X in each case representing oxygen, sulphur or an NH group or NCH$_3$ group and possible substituents in each case being: fluorine, chlorine, bromine, iodine, cyano, nitro, hydroxyl, methyl, ethyl, n- or i-propyl, n-, i-, s- or t-butyl, methoxy, ethoxy, n- or i-propoxy, methylthio, ethylthio, acetyl, propionyl, methylsulphinyl, methylsulphonyl, trifluoromethyl, trifluoromethoxy, trifluoromethylthio, trifluoromethylsulphinyl, trifluoromethylsulphonyl, chloroacetyl, dichloroacetyl, trifluoroacetyl, chloroethoxycarbonyl, phenyl, phenoxy, phenylthio, benzoyl, hydroxycarbonyl, methoxycarbonyl, ethoxycarbonyl, n- or i-propoxycarbonyl, allyloxycarbonyl, methoxymethoxycarbonyl, ethoxyethoxycarbonyl, hydroxyiminomethyl, methoxyiminomethyl, methoximinoethyl and ethoximinoethyl.

Especially preferred compounds of the general formula (I) are those in which
R$^1$ represents a methoxymethyl radical, and at the same time R$^2$ represents methyl, or
R$^2$ represents a methoxymethyl radical, and at the same time R$^1$ represents methyl,
R$^3$ represents hydrogen and
R$^4$ represents phenyl, α-naphthyl or β-naphthyl, in each case optionally mono-, di- or trisubstituted by identical or different substituents, or represents a heterocyclic radical of the formula

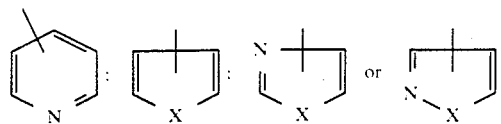

which is optionally mono-, di- or trisubstituted by identical or different substituents and/or benzo-fused, X in each case representing oxygen, sulphur or an NH group or NCH$_3$ group and possible substituents in each case being: fluorine, chlorine, bromine, iodine, cyano, nitro, hydroxyl, methyl, ethyl, methoxy, methylthio, acetyl, chloroethoxycarbonyl, trifluoromethyl, trifluoromethoxy, trifluoromethylthio, phenyl, phenoxy, phenylthio, hydroxycarbonyl, methoxycarbonyl, ethoxycarbonyl, allyloxycarbonyl, ethoxyethoxycarbonyl, hydroximinomethyl, methoxyiminomethyl and methoxyiminoethyl.

The following triazolo-pyrimidine-2-sulphonamides of the general formula (I) may be mentioned specifically, in addition to the compounds mentioned in the preparation examples:

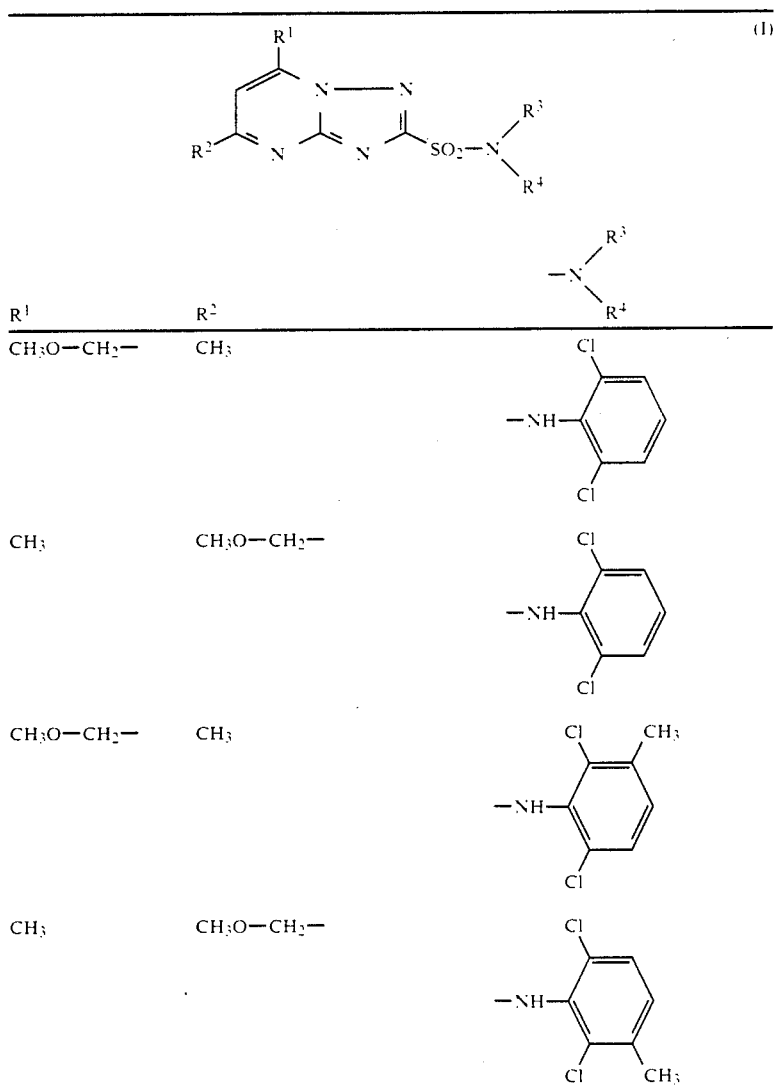

-continued
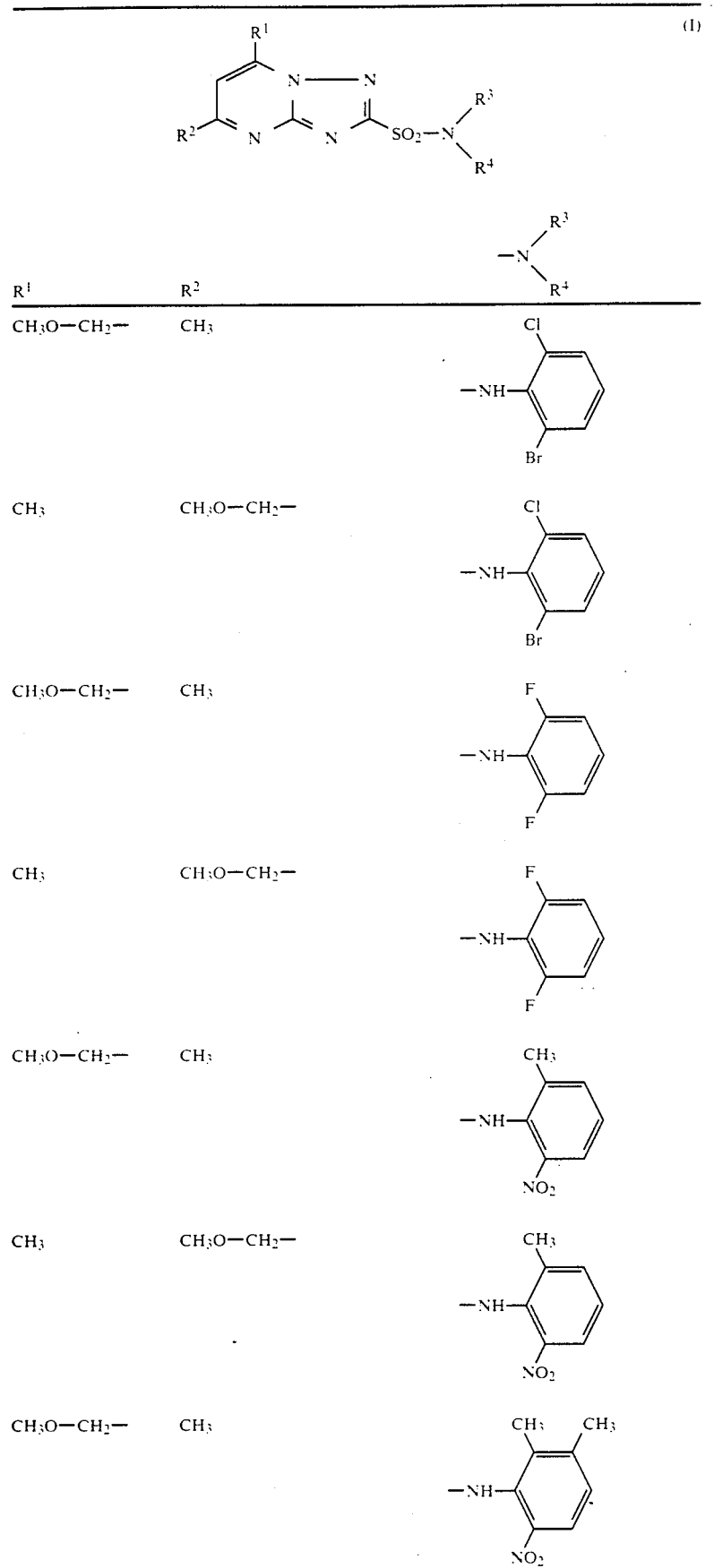
| R¹ | R² | —N(R³)(R⁴) |
|---|---|---|
| CH₃O—CH₂— | CH₃ | —NH—(2-Cl, 6-Br phenyl) |
| CH₃ | CH₃O—CH₂— | —NH—(2-Cl, 6-Br phenyl) |
| CH₃O—CH₂— | CH₃ | —NH—(2,6-diF phenyl) |
| CH₃ | CH₃O—CH₂— | —NH—(2,6-diF phenyl) |
| CH₃O—CH₂— | CH₃ | —NH—(2-CH₃, 6-NO₂ phenyl) |
| CH₃ | CH₃O—CH₂— | —NH—(2-CH₃, 6-NO₂ phenyl) |
| CH₃O—CH₂— | CH₃ | —NH—(2,3-diCH₃, 6-NO₂ phenyl) |

-continued
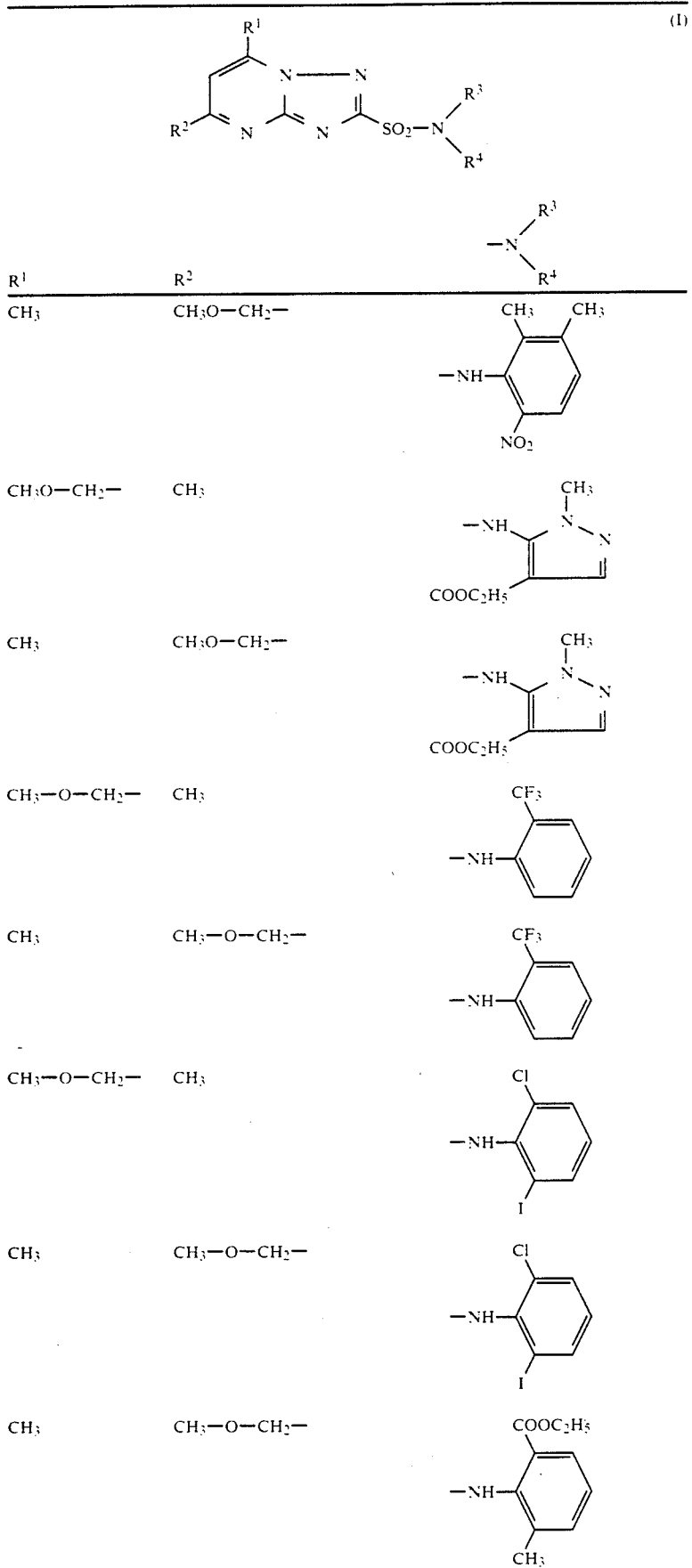
(I)
| R¹ | R² | -N(R³)(R⁴) |
|---|---|---|
| CH₃ | CH₃O—CH₂— | —NH-(2,6-dimethyl-3-nitrophenyl) |
| CH₃O—CH₂— | CH₃ | —NH-(1-methyl-4-ethoxycarbonylpyrazol-5-yl) |
| CH₃ | CH₃O—CH₂— | —NH-(1-methyl-4-ethoxycarbonylpyrazol-5-yl) |
| CH₃—O—CH₂— | CH₃ | —NH-(2-trifluoromethylphenyl) |
| CH₃ | CH₃—O—CH₂— | —NH-(2-trifluoromethylphenyl) |
| CH₃—O—CH₂— | CH₃ | —NH-(2-chloro-6-iodophenyl) |
| CH₃ | CH₃—O—CH₂— | —NH-(2-chloro-6-iodophenyl) |
| CH₃ | CH₃—O—CH₂— | —NH-(2-ethoxycarbonyl-6-methylphenyl) |

-continued
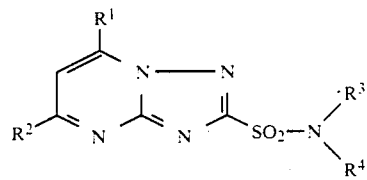
| R¹ | R² | −N(R³)(R⁴) |
|---|---|---|
| CH₃−O−CH₂− | CH₃ |  |
| CH₃−O−CH₂− | CH₃ | 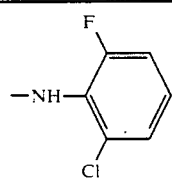 |
| CH₃−O−CH₂− | CH₃ | 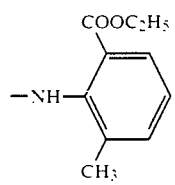 |
| CH₃ | CH₃−O−CH₂− | 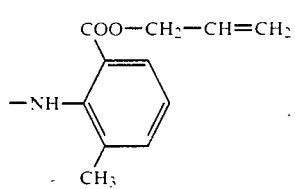 |
| CH₃−O−CH₂− | CH₃ | 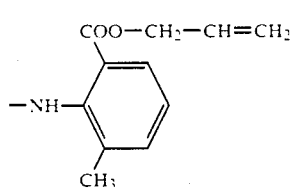 |
| CH₃ | CH₃−O−CH₂− | 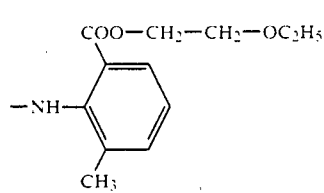 |
| CH₃ | CH₃−O−CH₂− | 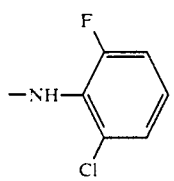 |
| CH₃ | CH₃−O−CH₂− | 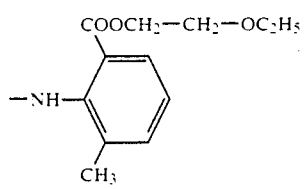 |

-continued
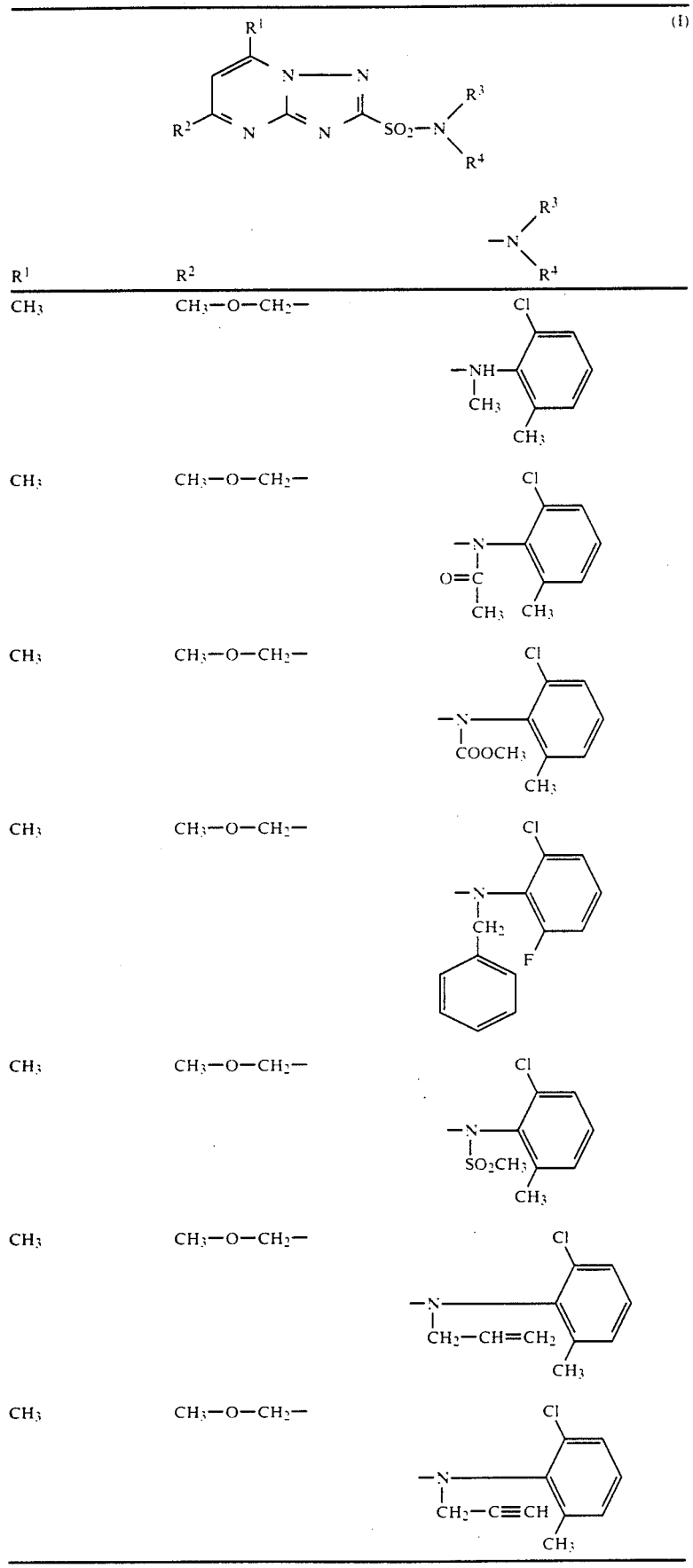
| $R^1$ | $R^2$ | $-N\begin{matrix}R^3\\R^4\end{matrix}$ |
|---|---|---|
| CH₃ | CH₃—O—CH₂— | 2-Cl-6-CH₃-phenyl-N(CH₃)H |
| CH₃ | CH₃—O—CH₂— | 2-Cl-6-CH₃-phenyl-N(COCH₃)— |
| CH₃ | CH₃—O—CH₂— | 2-Cl-6-CH₃-phenyl-N(COOCH₃)— |
| CH₃ | CH₃—O—CH₂— | 2-Cl-6-F-phenyl-N(CH₂C₆H₅)— |
| CH₃ | CH₃—O—CH₂— | 2-Cl-6-CH₃-phenyl-N(SO₂CH₃)— |
| CH₃ | CH₃—O—CH₂— | 2-Cl-6-CH₃-phenyl-N(CH₂—CH=CH₂)— |
| CH₃ | CH₃—O—CH₂— | 2-Cl-6-CH₃-phenyl-N(CH₂—C≡CH)— |

If, for example, 5-amino-3-(2,6-dichlorophenylaminosulphonyl)-1,2,4-triazole and methoxyacetylacetone are used as starting substances, the course of the reaction in process (a) according to the invention can be represented by the following equation:

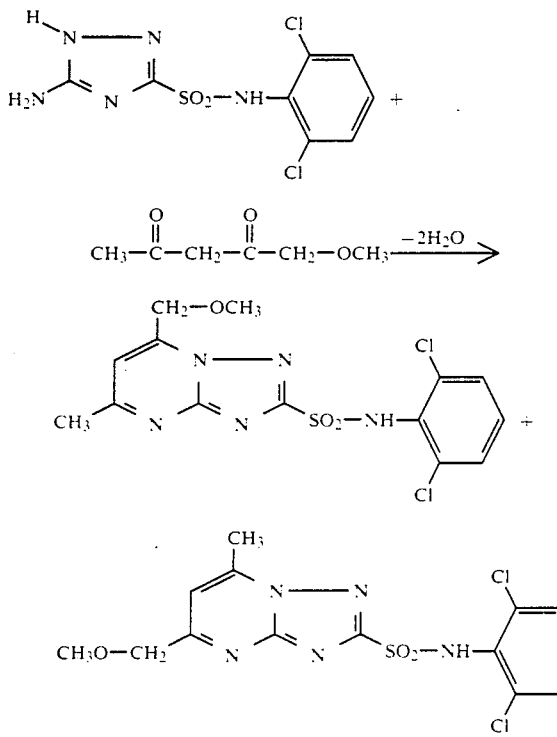

If, for example, 5-methoxymethyl-7-methyl-1,2,4-triazolo-[1,5-a]-pyrimidine-2-sulphonyl chloride and 2-chloro-6-methylaniline are used as starting substances, the course of the reaction in process (b) according to the invention can be represented by the following equation:

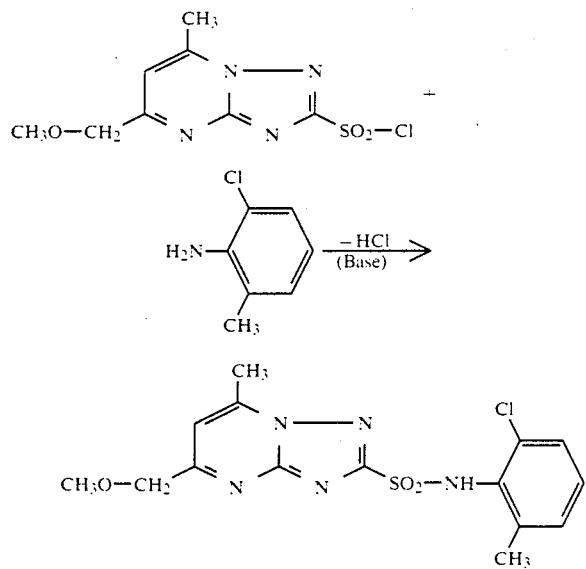

If, for example, 5-methyl-7-methoxymethyl-1,2,4-triazolo-[1,5-a]-pyrimidine-2-[N-(2,6-dimethylphenyl)]-sulphonamide and methyl iodide are used as starting substances, the course of the reaction in process (c) according to the invention can be represented by the following equation:

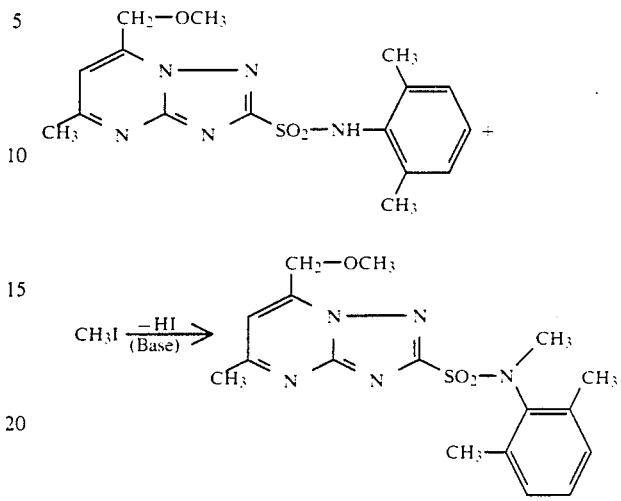

Formula (II) provides a general definition of the aminotriazolylsulphonamides required as starting substances for carrying out the process according to the invention. In this formula (II), $R^4$ preferably or particularly preferably represents those radicals which have already been mentioned as preferred or particularly preferred for this substituent in connection with the description of the substances of the formula (I) according to the invention. In formula (II), $R^4$ especially preferably represents those radicals which have been mentioned as especially preferred for this substituent in connection with the description of the substances of the formula (I) according to the invention.

The aminotriazolylsulphonamides of the formula (II) are not yet known.

They are obtained by a process in which 3-amino-5-benzylthio-1,2,4-triazole of the formula (VIIa)

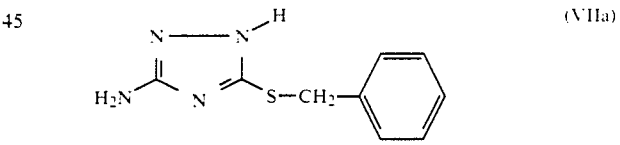

(See, for example, J. Heterocycl. Chem. 12, 1187 [1975]; and European Patent No. 142,152), which is in tautomeric equilibrium with the corresponding 5-amino-3-benzylthio compounds of the formula (VIIb)

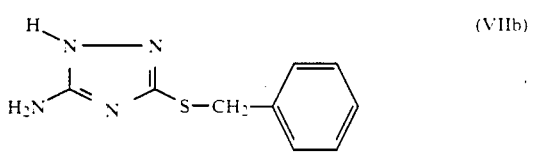

(VIIb)

is initially reacted in a 1st stage with phenyl chloroformate in the presence of a diluent, such as, for example, pyridine, at temperatures between −20° C. and +20° C., and the 1-phenoxycarbonyl-3-benzylthio-5-amino-1,2,4-triazole thus obtainable, of the formula (VIII)

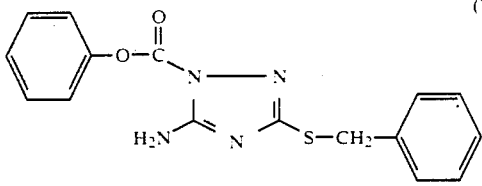

(VIII)

is reacted in a 2nd stage with elemental chlorine in the presence of water and in the presence of a diluent, such as, for example, chloroform, and in the presence of a reaction auxiliary, such as, for example, glacial acetic acid, at temperatures between −20° C. and +20° C., and the 5-amino-1-phenoxycarbonyl-1,2,4-triazol-3-yl-sulphonyl chloride obtainable in this way, of the formula (IX)

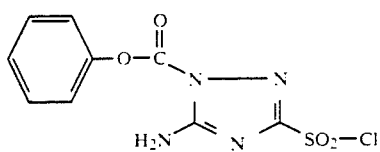

(IX)

is reacted in a 3rd stage with amines of the formula (V)

 $R^4-NH_2$ (V)

in which
$R^4$ has the abovementioned meaning,
if appropriate in the presence of a diluent, such as, for example, methylene chloride, and in the presence of an acid-binding agent, such as, for example, pyridine, and if appropriate in the presence of a reaction auxiliary, such as, for example, 4-dimethylaminopyridine, at temperatures between 0° C. and 60° C., and, in a 4th stage, the phenoxycarbonyl protective group in the 1-position of the triazole ring of the 5-amino-1-phenoxycarbonyl-1,2,4-triazol-3-yl-sulphonamides thus obtainable, of the formula (X)

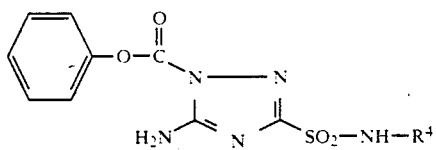

(X)

in which
$R^4$ has the abovementioned meaning,
is subsequently split off again with aqueous sodium hydroxide solution, if appropriate in the presence of a diluent, such as, for example, ethanol, at temperatures between 0° C. and 40° C.

The compounds of the formulae (VIII), (IX) and (X) are new and are likewise the subject of the present invention. They have a common structural element and can be described by the formula (XIV)

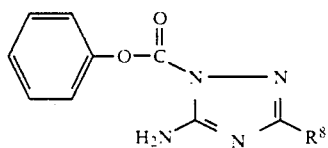

(XIV)

in which
$R^8$ represents benzylthio, $-SO_2Cl$ or $-SO_2-NH-R^4$, wherein
$R^4$ represents in each case optionally substituted aryl or heteroaryl.

In the formulae (X) and (XIV), $R^4$ preferably or particularly preferably or especially preferably represents those radicals which have already been mentioned as preferred or particularly preferred or especially preferred for this substituent in the description of the substances of the formula (I) according to the invention.

Formula (III) provides a general definition of the 1,3-diketones furthermore required as starting substances for carrying out process (a) according to the invention. In this formula (III), $R^5$ preferably represents those radicals which have already been mentioned as preferred for this substituent in connection with the description of the substances of the formula (I) according to the invention. $R^6$ preferably represents straight-chain or branched alkyl with 1 to 6 carbon atoms, in particular methyl, ethyl, n- or i-propyl or n-, i-, s- or t-butyl, especially methyl or ethyl.

The 1,3-diketones of the formula (III) are generally known compounds of organic chemistry or are obtainable by generally known processes analogously to known compounds (compare, for example, W. F. Bruce and H. W. Coover, J. Am. Chem. Soc. 66, 2092 [1944]).

Formula (IV) provides a general definition of the triazolo-pyrimidine-2-sulphonyl chlorides required as starting substances for carrying out process (b) according to the invention. In this formula (IV), $R^5$ and $R^6$ preferably in each case represent straight-chain or branched alkyl with 1 to 6 carbon atoms, in particular methyl, ethyl, n- or i-propyl or n-, i-, s- or t-butyl, especially methyl or ethyl.

The triazolo-pyrimidine-2-sulphonyl chlorides of the formula (IV) are not yet known and are the subject of the present invention.

They are obtained by a process in which 5-amino-1,2,4-triazole derivatives of the formula (VII)

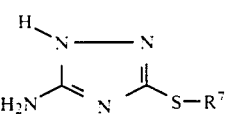

(VII)

in which
$R^7$ represents hydrogen, or represents a benzyl radical, are initially subjected to a condensation reaction with 1,3-diketones of the formula (III)

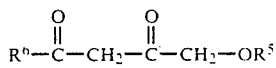

(III)

in which
$R^5$ and $R^6$ have the abovementioned meaning,
in a 1st stage analogously to process (a) according to the invention, if appropriate in the presence of a dilutent, such as, for example, glacial acetic acid, at temperatures between 20° C. and 120° C., and the position isomer mixture of triazolopyrimidine derivatives obtainable in this manner, of the formulae (XIa) and (XIb)

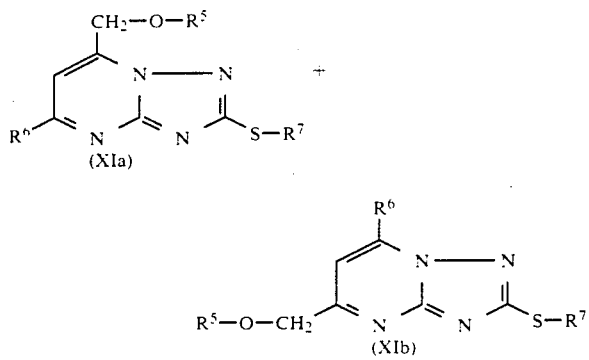

in which
R⁵, R⁶ and R⁷ have the abovementioned meaning,
are reacted in a 2nd stage with elemental chlorine in the presence of water and if appropriate in the presence of a diluent, such as, for example, chloroform, at temperatures between −20° C. and +20° C.

The mixture obtainable in this manner, of the desired triazolo-pyrimidine-2-sulphonyl chloride of the formula (IV)

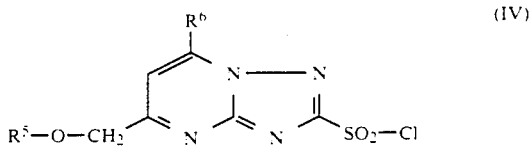

and a compound chlorinated in the 6-position on the nucleus, of the formula (XII)

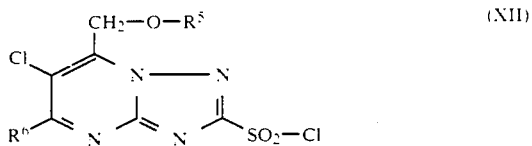

wherein, in the two formulae (IV) and (XII),
R⁵ and R⁶ have the abovementioned meanings,
can be used without further separation as the starting compound for carrying out process (b) according to the invention.

The 5-amino-1,2,4-triazole derivatives of the formulae (VII), (VIIa) and (VIIb) are known (see, for example, European Patent No. 142,152).

The triazolopyrimidine derivatives of the formulae (XIa) and (XIb) are new and are the subject of the present invention. In these formulae (XIa) and (XIb), R⁵ and R⁶ preferably represent straight-chain or branched alkyl with 1 to 6 carbon atoms, in particular methyl, ethyl, n- or i-propyl or n-, i-, s- or t-butyl, especially methyl or ethyl.

The formulae (IV), (XIa) and (XIb) have a common structural element and can therefore be described by the formula (XV)

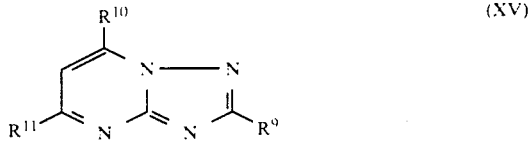

in which
R⁹ represents —SO₂Cl or —S—R⁷,
wherein
R⁷ represents hydrogen, or represents a benzyl radical,
R¹⁰ represents R⁶ and
R¹¹ represents —CH₂—O—R⁵, or in the case where R represents —S—R⁷,
R¹⁰ also represents —CH₂—O—R⁵ and
R¹¹ represents R⁶,
wherein
R⁵ and R⁶ have the abovementioned meaning.

Formula (V) provides a general definition of the amines furthermore required as starting substances for carrying out process (b) according to the invention. In this formula (V), R⁴ preferably represents those radicals which have already been mentioned as preferred for this substituent in connection with the description of the substances of the formula (I) according to the invention.

The amines of the formula (V) are generally known compounds of organic chemistry.

Formula (Ia) provides a general definition of the triazolo-pyrimidine-2-sulphonamides required as starting substances for carrying out process (c) according to the invention. In this formula (Ia), R¹, R² and R⁴ preferably represent those radicals which have already been mentioned as preferred for these substituents in connection with the description of the substances of the formula (I) according to the invention.

The triazolo-pyrimidine-2-sulphonamides of the formula (Ia) are compounds according to the invention and are obtainable with the aid of processes (a) or (b) according to the invention.

Formula (VI) provides a general definition of the alkylating, acylating or sulphonylating agents furthermore required as starting substances for carrying out process (c) according to the invention. In this formula (VI), R³⁻¹ preferably represents in each case straight-chain or branched alkyl, alkylcarbonyl, alkoxycarbonyl or alkylsulphonyl with in each case 1 to 4 carbon atoms in the individual alkyl parts, or represents in each case straight-chain or branched alkenyl or alkinyl with in each case 3 to 6 carbon atoms, or represents aralkyl which has 1 to 4 carbon atoms in the alkyl part and 6 to 10 carbon atoms in the aryl part and is straight-chain or branched in the alkyl part and optionally monosubstituted or polysubstituted by identical or different substituents in the aryl part, possible substituents on the aryl being: fluorine, chlorine, bromine, iodine, cyano, nitro, hydroxyl and in each case straight-chain or branched alkyl, alkoxy, alkylthio, halogenoalkyl, halogenoalkoxy and halogenoalkylthio with in each case 1 to 4 carbon atoms and where appropriate 1 to 9 identical or different halogen atoms; R³⁻¹ in particular represents methyl, ethyl, acetyl, methoxycarbonyl, ethoxycarbonyl, methylsulphonyl, allyl, propargyl or benzyl. Y preferably represents halogen, in particular chlorine, bromine or iodine.

The alkylating, acylating or sulphonylating agents of the formula (VI) are generally known compounds of organic chemistry.

Possible diluents for carrying out process (a) according to the invention are inert organic solvents. Polar organic solvents, for example higher-boiling alcohols, such as ethylene glycol monoethyl ether, ethanol, propanol or butanol, or carboxylic acids, such as, for example, acetic acid, are especially preferably used.

The reaction temperatures can be varied within a substantial range in carrying out process (a) according to the invention. The reaction is in general carried out at temperatures between 20° C. and 200° C., preferably at temperatures between 50° C. and 150° C.

For carrying out the process (a) according to the invention, in general 1.0 to 3.0 mol, preferably 1.0 to 2.0 mol, of 1,3-diketone of the formula (III) are employed per mol of aminotriazolylsulphonamide of the formula (II). The reaction is carried out and the reaction products of the formula (I) are worked up and isolated by a process analogous to known processes (see, for example, European Patent No. 142,152). As a rule, position isomer mixtures of the triazolopyrimidine-2-sulphonamides of the formulae (Ia1) and (Ib)

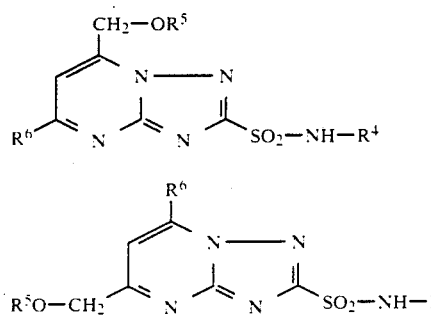

wherein
$R^4$, $R^5$ and $R^6$ in each case have the above-mentioned meaning,
are thereby obtained.

These mixtures can be separated into their constituents with the aid of customary separation methods (chromatography or crystallization). However, it is also possible for the mixtures as such to be used according to the invention.

Possible diluents for carrying out process (b) according to the invention are likewise inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

Process (b) according to the invention is preferably carried out in the presence of a suitable acid-binding agent. Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

It is also possible for the amine of the formula (V) used as the reaction partner to be simultaneously used in a corresponding excess as the acid-binding agent.

The reaction temperatures can be varied within a substantial range in carrying out process (b) according to the invention. The reaction is in general carried out at temperatures between 0° C. and 150° C., preferably at temperatures between 10° C. and 80° C.

For carrying out process (b) according to the invention, in general 1.0 to 5.0 mol, preferably 1.0 to 2.0 mol, of amine of the formula (V) and if appropriate 1.0 to 2.0 mol of acid-binding agent are employed per mol of triazolo-pyrimidine-2-sulphonyl chloride of the formula (IV). In a preferred embodiment, the triazolopyrimidine-2-sulphonyl chloride of the formula (VI) suitable as the starting substance is used as the starting compound in a crude product mixture together with the 6-chloro-triazolo-pyrimidine-2-sulphonyl chloride simultaneously formed, of the formula (XII)

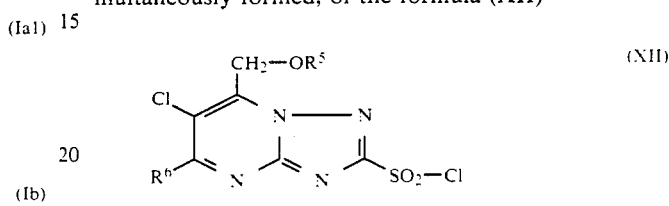

(wherein $R^5$ and $R^6$ have the abovementioned meaning). The corresponding end products of the formulae (Ib) and (XIII)

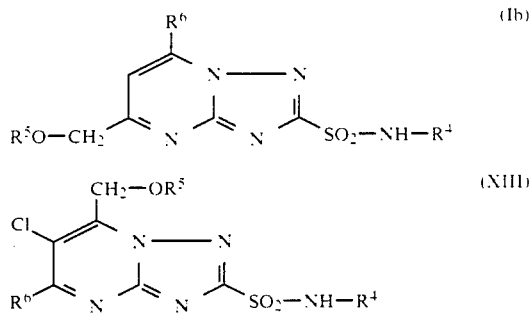

(wherein $R^4$, $R^5$ and $R^6$ in each case have the abovementioned meaning) are separated with the aid of customary separation processes, for example by chromatography (in this context compare also the preparation examples).

Possible diluents for carrying out process (c) according to the invention are likewise inert organic solvents. The solvents mentioned for process (b) are preferably used.

Process (c) according to the invention is preferably carried out in the presence of a basic reaction auxiliary. Possible basic reaction auxiliaries are all the customary inorganic or organic bases. The hydroxides, carbonates or amines mentioned for process (b) are preferably used.

The reaction temperatures can be varied within a substantial range in carrying out process (c) according to the invention. The reaction is in general carried out at temperatures between −20° C. and +150° C., preferably at temperatures between 0° C. and +120° C.

For carrying out process (c) according to the invention, in general 1.0 to 5.0 mol, preferably 1.0 to 2.0 mol, of alkylating, acylating or sulphonylating agent of the formula (VI) and if appropriate 1.0 to 5.0 mol, preferably 1.0 to 2.0 mol, of basic reaction auxiliary are employed per mol of triazolo-pyrimidine-2-sulphonamide of the formula (Ia). The reaction is carried out and the reaction products of the formula (Ic) are worked up and isolated by a process analogous to generally customary processes.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicolyledon cultures of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for combating mono- and dicotyledon weeds by the pre- and post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea, for combating weeds in cereals; 4-amino-3-methyl-6-phenyl-1,2,4-triazin-5-(4H)-one, for combating weeds in sugar beet, and 4-amino-6-(1,1-dimethylethyl)-3-methylthio-1,2,4-triazin-5(4H)-one, for combating weeds in soya beans.

Mixtures with N,N-dimethyl-N'-(3-chloro-4-methylphenyl)-urea; N,N-dimethyl-N'-(4-isopropylphenyl)-urea; 2-chloro-4-ethylamino-6-isopropylamino-1,3,5-triazine; 4-ethylamino-2-t-butylamino-6-methylthio-s-triazine; 2-chloro-4-ethylamino-6-(3-cyanopropylamino)-1,3,5-triazine; 4-amino-6-t-butyl-3-ethylthio-1,2,4-triazin-5(4H)-one; N-methyl-2-(1,3-benzothiazol-2-yloxy)-acetanilide; N-(methoxymethyl)-2,6- diethyl-chloroacetanilide; 2-ethyl-6-methyl-N-(1-methyl-2-methoxyethyl)-chloroacetanilide; 2-chloro-N-(2,6-dimethylphenyl)-N-[(1H)-pyrazol-1-yl-methyl]-acetamide; α-chloro-2',6'-diethyl-N-(2-propoxyethyl)-acetanilide; S-(2,3,3-trichloroallyl) N,N-diisopropyl-thiolcarbamate; S-ethyl N,N-hexamethylenethiolcarbamate; 2,6-dinitro-4-trifluoromethyl-N,N-di-propylaniline; N-(1-ethylpropyl)-3,4-dimethyl-2,6-di-nitroaniline; 2-chloro-N-{[(4-methoxy-6-methyl-1,3,5-triazin-2-yl)-amino]-carbonyl}-benzenesulphonamide; 2-{[[((4-methoxy-6-methyl-1,3,5-triazin-2-yl)-amino)-carbonyl]-amino]-sulphonyl}-benzoic acid or the methyl ester thereof; ethyl 2-{[(4-chloro-6-methoxy-2-pyrimidinyl)-aminocarbonyl]-aminosulphonyl}-benzoate; methyl 2-[4-(2,4-dichlorophenoxy)-phenoxy]-propionate; 2-{4-[(3-chloro-5-trifluoromethyl-2-pyridinyl)-oxy]-phenoxy}-propanoic acid or -propanoic acid ethyl ester; methyl 5-(2,4-dichlorophenoxy)-2-nitrobenzoate; 5-(2-chloro-4-trifluoromethyl-phenoxy)-2-nitro-benzoic acid; 3,5-diiodo-4-hydroxybenzonitrile; 3,5-dibromo-4-hydroxy-benzonitrile; 2-[5-methyl-5-(1-methylethyl)-4-oxo-2-imidazolin-2-yl]-3-quinolinecarboxylic acid; methyl 2-[4,5-dihydro-4-methyl-4-(1-methylethyl)-5-oxo-1H-imidazol-2-yl]-4(5)-methylbenzoate; exo-1-methyl-4-(1-methylethyl)-2-(2-methylphenyl-methoxy)-7-oxabicyclo-(2,2,1)-heptane; 2,4-dichlorophenoxyacetic acid; 2,4-dichlorophenoxypropionic acid; (4-chloro-2-methylphenoxy)-propionic acid; (2-methyl-4-chlorophenoxy)-acetic acid; 0-(6-chloro-3-phenyl-pyridazin-4-yl) S-octyl thiocarbonate or 3-isopropyl-2,1,3-benzothiadiazin-4-one 2,2-dioxide are also possible. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

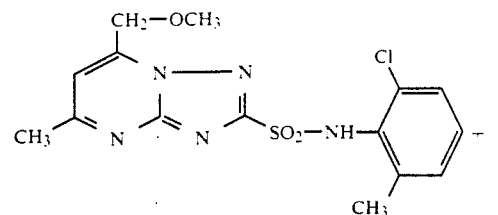
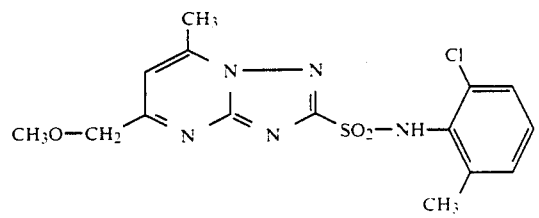

Process a 5.0 g (0.0174 mol) of 5-amino-1,2,4-triazol-3-yl N-(2-chloro-6-methyl-phenyl)-sulphonamide and 2.9 g (0.0223 mol) of methoxyacetylacetone are heated under reflux in 30 ml of glacial acetic acid for one hour. The cooled reaction mixture is concentrated in vacuo and the residue is stirred with ether. The solid which has precipitated out is filtered off with suction and dried. 5.7 g (86% of theory) of a mixture of 5-methyl-7-methoxymethyl-N-(2-chloro-6-methylphenyl)-1,2,4-triazolo-[1,5-a]-pyrimidine-2-sulphonamide (70%) and 7-methyl-5-methoxymethyl-N-(2-chloro-6-methyl-phenyl)-1,2,4-triazolo-[1,5-a]-pyrimidine-2-sulphonamide (30%) of melting point 203° C. are obtained.

EXAMPLE 2

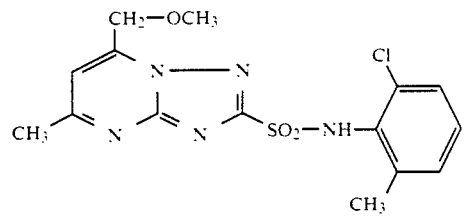

2.0 g (30% of theory) of 5-methyl-7-methoxymethyl-N-(2-chloro-6-methyl-phenyl)-1,2,4-triazolo-[1,5-a]-pyrimidine-2-sulphonamide of melting point 227° C. are obtained from the position isomer mixture of the compounds (Example 1) by several recrystallizations.

EXAMPLE 3

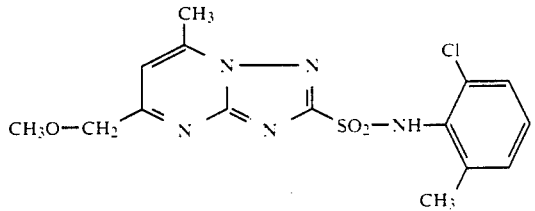

Process b 2.7 g (about 0.0095 mol) of a crude product mixture of 6-chloro-5-methyl-7-methoxymethyl-1,2,4-triazolo-[1,5-a]-pyrimidine-2-sulphonyl chloride and 7-methyl-5-methoxymethyl-1,2,4-triazolo-[1,5-a]-pyrimidine-2-sulphonyl chloride in 5 ml of dry methylene chloride are added to 1.35 g (0.00935 mol) of 2-chloro-6-methylaniline, 0.75 g (0.0095 mol) of absolute pyridine and 0.12 g (0.001 mol) of 4-dimethylaminopyridine in 50 ml of dry methylene chloride and the mixture is stirred at room temperature for 15 hours, washed with water, dried over sodium sulphate and concentrated in vacuo. The oily residue is separated by chromatography (silica gel; mobile phase: methylene chloride/acetone 4:1). 0.7 g (19% of theory, based on the precursor 5(7)-methyl-7(5)-methoxymethyl-2-mercapto-1,2,4-triazolo-[1,5-a]-pyrimidine employed) of 7-methyl-5-methoxymethyl-N-(2-chloro-6-methylphenyl)-1,2,4-triazolo-[1,5-a]-pyrimidine-2-sulphonamide of melting point 169° C. is obtained as the 2nd fraction.

0.5 g (12% of theory, based on the precursor 5(7)-methyl-7(5)-methoxymethyl-2-mercapto-1,2,4-triazolo-[1,5-a]-pyrimidine employed) of 6-chloro-5-methyl-7-methoxymethyl-N-(2-chloro-6-methylphenyl)-1,2,4-triazolo-[1,5-a]-pyrimidine-2-sulphonamide of melting point 244° C. (decomposition) is eluted first as a by-product.

The following triazolo-pyrimidine-2-sulphonamides of the general formula (I) are obtained in a corresponding manner and in accordance with the general statements on the preparation:

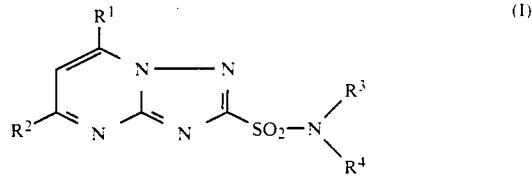

(I)

TABLE 1

| Example No. | R¹ | R² | $-N\begin{smallmatrix}R^3\\R^4\end{smallmatrix}$ | Melting Point °C. |
|---|---|---|---|---|
| 4 | CH₃ (CH₃O—CH₂—) | CH₃O—CH₂— (CH₃) | —NH—C₆H₃(CH₃)(COOCH₃) | Oil ¹H-NMR*: 4.67 and 4.85. |
| 5 | CH₃O—CH₂— | CH₃ | —NH—C₆H₃(CH₃)(COOCH₃) | 102–105 |
| 6 | CH₃O—CH₂— | CH₃ | —N(COCH₃)—C₆H₃(CH₃)(Cl) | 195 (decomp.) |
| 7 | CH₃O—CH₂— | CH₃ | —N(SO₂CH₃)—C₆H₃(CH₃)(Cl) | 192 (decomp.) |
| 8 | CH₃O—CH₂— | CH₃ | —N(COOCH₃)—C₆H₃(CH₃)(Cl) | 167 (decomp.) |
| 9 | CH₃O—CH₂— | CH₃ | —NH—C₆H₄(Cl) | 153–155 |

TABLE 1-continued

| Example No. | R¹ | R² | —N(R³)(R⁴) | Melting Point/°C |
|---|---|---|---|---|
| 10 | $CH_3O-CH_2-$ | $CH_3$ | —NH-(2-methyl-6-(COO-CH₂-CH₂-Cl))phenyl | Oil ¹H-NMR*: 4.87 |
| 11 | $CH_3O-CH_2-$ | $CH_3$ | —NH-(2-Br-6-CH₃)phenyl | 214–216 |

$$\text{(I)} \quad \underset{R^2}{\underset{|}{\overset{R^1}{\overset{|}{\diagdown}}}}\!\!\!\!\begin{array}{c}N\!\!\!=\!\!\!\!\diagup\!\!\!\!\!\diagdown\!\!\!\!N\!\!-\!\!\!N\\ \diagup\!\!\!\!\!\!\diagdown\;\;\;\;\;\;\;\diagdown\!\!\!\!\diagup\\ N\;\;\;\;\;\;\;\;\;N\end{array}\!\!-\!SO_2-N(R^3)(R^4)$$

| Example No. | R¹ | R² | —N(R³)(R⁴) | Melting Point/°C |
|---|---|---|---|---|
| 12 | $CH_3O-CH_2-$ ($CH_3$) | $CH_3$ ($CH_3O-CH_2-$) | —NH-(2-methyl-6-(COOC₂H₅))phenyl | 97–104 |
| 13 | $CH_3O-CH_2-$ | $CH_3$ | —NH-(2-CONH₂)phenyl | 215–217 |
| 14 | $CH_3O-CH_2-$ | $CH_3$ | —NH-(2-OCH₃)phenyl | 149–151 |
| 15 | $C_2H_5O-CH_2-$ | $CH_3$ | —NH-(2-Cl-6-CH₃)phenyl | 199–200 |
| 16 | $C_2H_5O-CH_2-$ | $CH_3$ | —NH-(2-OCH₃)phenyl | 135–137 |

TABLE 1-continued $$-N{\overset{R^3}{\underset{R^4}{}}}$$

| Example No. | R¹ | R² | -NR³R⁴ | Melting Point/°C. |
|---|---|---|---|---|
| 17 | CH₃O—CH₂— | CH₃ | —NH—(2-Cl, 6-CH₃O-phenyl) | 206 |
| 18 | CH₃O—CH₂— | CH₃ | —NH—(2-Br-phenyl) | 132–134 |
| 19 | CH₃O—CH₂— | CH₃ | —NH—(2,6-di-CH₃-phenyl) | 245–247 |
| 20 | CH₃O—CH₂— (CH₃) | CH₃ (CH₃O—CH₂—) | —NH—(4-Cl, 2-CH₃O-phenyl) | 166–172 |
| 21 | CH₃O—CH₂— (CH₃) | CH₃ (CH₃O—CH₂—) | —NH—(2-CH₃, 3-Cl-phenyl) | 133–138 |
| 22 | CH₃O—CH₂— | CH₃ | —NH—(2-Cl, 5-CH₃-phenyl) | 168–172 |
| 23 | CH₃ | CH₃O—CH₂— | —NH—(2-CONH₂-phenyl) | 170–173 |
| 24 | CH₃O—CH₂— (CH₃) | CH₃ (CH₃O—CH₂—) | —NH—(2,3-di-CH₃-phenyl) | 164–168 |
| 25 | CH₃O—CH₂— | CH₃ | —NH—(2,5-di-CH₃-phenyl) | 169–171 |

TABLE 1-continued

| Example No. | $R^1$ | $R^2$ | $-N\begin{smallmatrix}R^3\\R^4\end{smallmatrix}$ | Melting Point/°C. |
|---|---|---|---|---|
| 26 | $CH_3O-CH_2-$ | $CH_3$ | (-NH- phenyl with o-CH₃O and N-C(=O)-CH₃) | 208 |
| 27 | $CH_3O-CH_2-$ ($CH_3$) | $CH_3$ ($CH_3O-CH_2-$) | $-NH-$ phenyl with o-$CH_3S$ | 123-131 |
| 28 | $CH_3O-CH_2-$ ($CH_3$) | $CH_3$ ($CH_3O-CH_2-$) | $-NH-$ phenyl with $OCH_3$ and $CH_3O$ | 129-130 |

*The $^1$H-NMR spectra were recorded in $CDCl_3$ with TMS (tetramethylsilane) as the internal standard. The chemical shift as the δ value in ppm is quoted.

PREPARATION OF THE PRECURSORS

EXAMPLE II—1

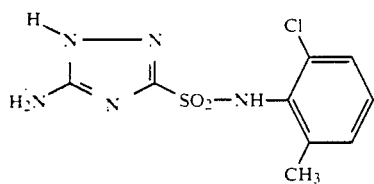

14.9 g (0.168 mol) of 45 percent strength aqueous sodium hydroxide solution are added to 34.1 g (0.0837 mol) of 5-amino-1-phenoxycarbonyl-1,2,4-triazol-3-yl-[N-(2-chloro-6-methyl-phenyl)]-sulphonamide in 350 ml of ethanol and the mixture is stirred at room temperature for one hour, acidified with glacial acetic acid and concentrated in vacuo. The residue is washed three times with water and then dried at 80° C. in vacuo. The solid thus obtained is purified by stirring with diethyl ether.

13.5 g (56% of theory) of 5-amino-1,2,4-triazol-3-yl-[N-(2-chloro-6-methyl-phenyl)]-sulphonamide of melting point 217° C. are obtained.

In an analogous manner the following compounds are obtainable:

EXAMPLE II—2

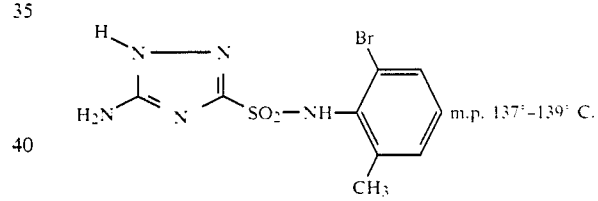

m.p. 137°-139° C.

EXAMPLE II—3

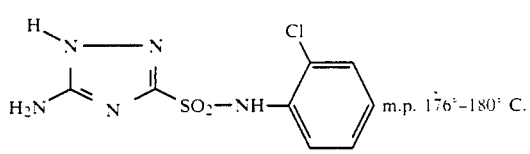

m.p. 176°-180° C.

EXAMPLE II—4

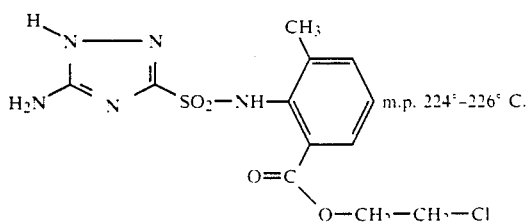

m.p. 224°-226° C.

EXAMPLE X—1

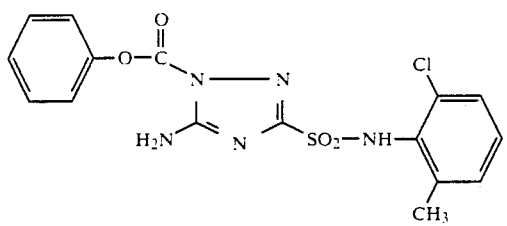

27.9 g (0.0922 mol) of 5-amino-1-phenoxycarbonyl-1,2,4-triazol-3-yl-sulphonyl chloride are added to 7.3 g (0.0922 mol) of absolute pyridine, 13 g (0.092 mol) of 2-chloro-6-methylaniline and 1.1 g (0.009 mol) of 4-dimethylaminopyridine in 300 ml of dry methylene chloride, the mixture is stirred at room temperature for one hour, the solvent is removed in vacuo, the oily residue is stirred with water, the mixture is decanted and the oil which remains is recrystallized from ethanol.

35.5 g (95% of theory) of 5-amino-1-phenoxycarbonyl-1,2,4-triazol-3-yl-[N-(2-chloro-6-methylphenyl)]-sulphonamide of melting point 200° C. are obtained.

In an analogous manner the following compounds are obtainable:

EXAMPLE X—2

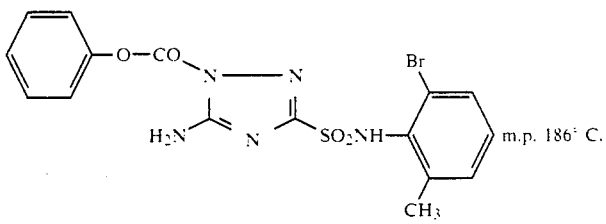

m.p. 186° C.

EXAMPLE X—3

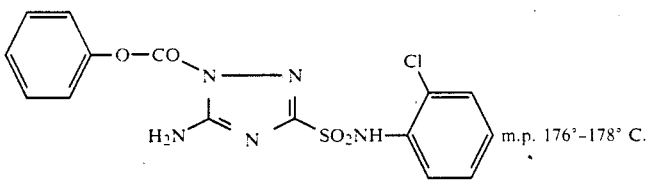

m.p. 176°-178° C.

EXAMPLE X—4

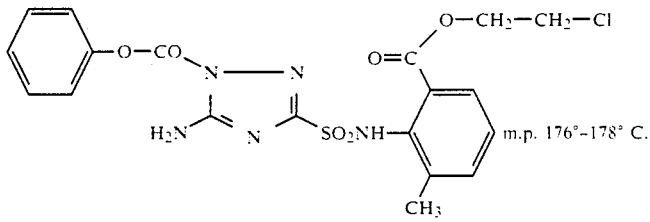

m.p. 176°-178° C.

EXAMPLE IX

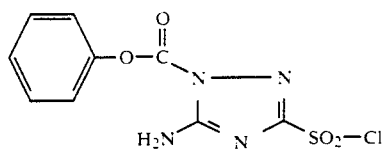

30 ml of glacial acetic acid and 15 ml of water are added to 136.6 g (0.419 mol) of 5-amino-1-phenoxycarbonyl-3-benzylthio-1,2,4-triazole in 1,700 ml of chloroform and a stream of chlorine gas which has not been dried is passed through this suspension at −5° C. for one hour, a clear solution being formed.

For working up, the solvent is removed in vacuo and the residue is stirred with 1 l of ether. The etherinsoluble solid is filtered off with suction and dried.

101 g (80% of theory) of 5-amino-1-phenoxycarbonyl-1,2,4-triazol-3-yl-sulphonyl chloride of melting point 164° C. are obtained.

EXAMPLE VIII

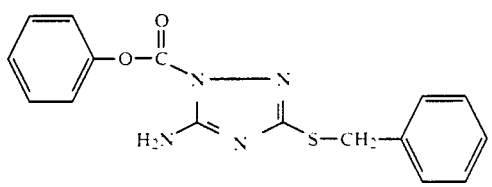

83.6 g (0.5339 mol) of phenyl chloroformate are added dropwise to 100 g (0.4854 mol) of 3-amino-5-benzylthio-1,2,4-triazole (see J. Het. Chem. 12, 1187 [1975])

in 700 ml of absolute pyridine, with cooling, so that the internal temperature does not rise above 5° C. When the addition has ended, stirring is continued at 10° C. for a further 60 minutes, the reaction mixture is then poured into ice-water and the solid which has precipitated out is filtered off with suction and recrystallized from ethanol.

140 g (88.5% of theory) of 5-amino-3-benzylthio-1-phenoxycarbonyl-1,2,4-triazole of melting point 285° C. (decomposition) are obtained.

EXAMPLE IV—1/XII—1

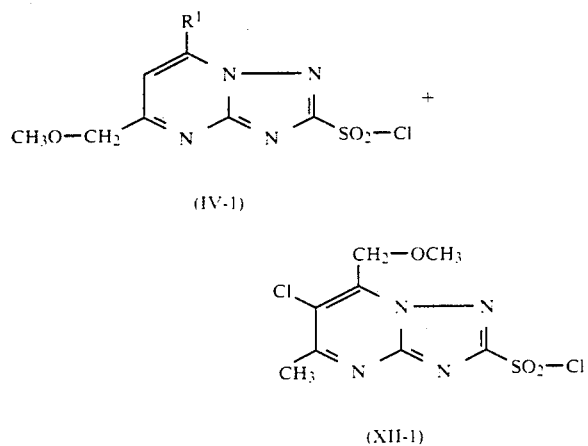

0.5 ml of water is added to 2 g (0.0095 mol) of a 1:1 mixture of 5-methyl-7-methoxymethyl-2-mercapto-1,2,4-triazolo-[1,5-a]-pyrimidine and 7-methyl-5-methoxymethyl-2-mercapto-1,2,4-triazolo-[1,5-a]-pyrimidine in 150 ml of chloroform, and a stream of chlorine gas which has not been dried is passed through this suspension at −5° C. for about 30 minutes, a clear solution being formed. For working up, the solvent is removed in vacuo and the colourless oil thus obtained is used in the next stage without further purification.

EXAMPLE XIa—1/XIb—1

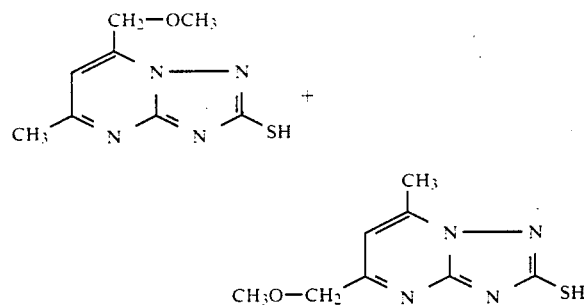

10.0 g (0.086 mol) of 3-amino-5-mercapto-1,2,4-triazole and 13.4 g (0.103 mol) of methoxyacetylacetone in 100 ml of glacial acetic acid are heated under reflux for 90 minutes. The product is precipitated in crystalline form from the cooled reaction mixture.

12 g (66% of theory) of a mixture of 5-methyl-7-methoxymethyl-3-mercapto-1,2,4-triazolo-[1,5-a]-pyrimidine (50%) and 7-methyl-5-methoxymethyl-3-mercapto-1,2,4-triazolo-[1,5a]-pyrimidine (50%) of melting point 209° C. are obtained.

USE EXAMPLES

The compound shown below was employed as the comparison substance in the use examples which follow:

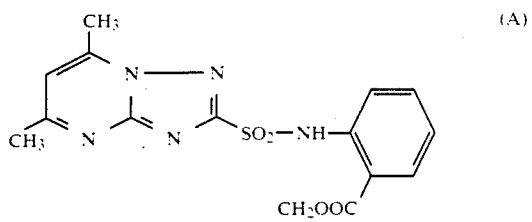

5,7-Dimethyl-N-(2-methoxycarbonyl-phenyl)-1,2,4-triazolo-[1,5-a]-pyrimidine-2-sulphonamide (known from European Patent 142,152/compound 10)

EXAMPLE A

Pre-emergence test: Solvent: 5 parts by weight of acetone. Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, a clearly superior herbicidal activity against mono- and dicotyledon weeds to comparison compound (A) is shown, for example, by the compounds according to preparation examples 1, 2, 3, 4, 5, 6, 7 and 8.

EXAMPLE B

Post-emergence test: Solvent: 5 parts by weight of acetone. Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2.000 l of water/ha. After three weeks, the degree of damage to the plants is rated in % damage in comparison to the development of the untreated control. The figures denote:

0% = no action (like untreated control)

100% = total destruction

In this test, a herbicidal activity against mono— and dicotyledon weeds which is clearly superior to comparison compound (A) is shown, for example, by the compounds according to preparation examples 1, 2, 3, 4, 5, 6, 7 and 8.

What is claimed is:

1. A triazolo-pyrimidine-2-sulphonamide of the formula

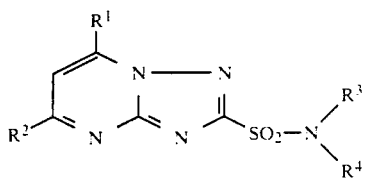

in which

R$^1$ represents —CH$_2$—O—R$^5$, and at the same time R$^2$ represents straight-chain or branched alkyl with 1 to 6 carbon atoms, or R$^2$ represents —CH$_2$—O—R$^5$, and at the same time R$^1$ represents straight-chain or branched alkyl with 1 to 6 carbon atoms, wherein R$^5$ in both cases represents straight-chain or branched alkyl with 1 to 6 carbon atoms, R$^3$ represents hydrogen, or represents in each case straight-chain or branched alkyl, alkylcarbonyl, alkoxycarbonyl or alkylsulphonyl with in each case 1 to 4 carbon atoms in the individual alkyl parts, or represents in each case straight-chain or branched alkenyl or alkinyl with in each case 3 to 6 carbon atoms, or represents aralkyl which has 1 to 4 carbon atoms in the alkyl part and 6 to 10 carbon atoms in the aryl part and is straight-chain or branched in the alkyl part and optionally monosubstituted or polysubstituted by identical or different substituents in the aryl part said substituents being fluorine, chlorine, bromine, iodine, cyano, nitro, hydroxyl and in each case straight-chain or branched alkyl, alkoxy, alkylthio, halogenoalkyl, halogenoalkoxy and halogenoalkylthio with in each case 1 to 4 carbon atoms and if appropriate 1 to 9 identical or different halogen atoms, and R$^4$ represents aryl which has 6 to 10 carbon atoms and is optionally monosubstituted or polysubstituted by identical or different substituents, or represents a 5— to 7—membered heterocyclic radical which has 1 to 3 hetero atoms, said hetero atoms being nitrogen, oxygen and/or sulphur, and is optionally monosubstituted or polysubstituted by identical or different substituents and/or benzo-fused, said substituents in each case being fluorine, chlorine, bromine, iodine, cyano, nitro, hydroxyl, in each case straight-chain or branched alkyl, alkoxy, alkylthio, alkylcarbonyl, alkylsulphinyl and alkylsulphonyl with in each case 1 to 6 carbon atoms, in each case straight-chain or branched halogenoalkyl, halogenoalkoxy, halogenoalkylthio, halogenoalkylsulphinyl, halogenoalkylsulphonyl, halogenoalkylcarbonyl or halogenoalkoxycarbonyl with in each case 1 to 6 carbon atoms and 1 to 9 identical or different halogen atoms, phenyl, phenoxy, phenylthio, phenylcarbonyl, hydroxycarbonyl, in each case straight-chain or branched alkoxycarbonyl, alkenyloxycarbonyl and alkoxy-alkoxycarbonyl with in each case 1 to 6 carbon atoms in the individual alkyl parts and 3 to 6 carbon atoms in the alkenyl part, and hydroximinoalkyl and straight-chain or branched alkoximinoalkyl with in each case 1 to 4 carbon atoms in the individual alkyl parts.

2. A triazolo-pyrimidine-2-sulphonamide according to claim 1, in which

R$^1$ represents —CH$_2$—O—CH$_3$ or —CH$_2$—O—C$_2$H$_5$, and at the same time R$^2$ represents methyl or ethyl, or R$^2$ represents —CH$_2$—O—CH$_3$ or —CH$_2$—O—C$_2$H$_5$, and at the same time R$^1$ represents methyl or ethyl, R$^3$ represents hydrogen, methyl, ethyl, acetyl, methoxycarbonyl, ethoxycarbonyl, methylsulphonyl, allyl, propargyl or benzyl and R$^4$ represents phenyl or naphthyl, in each case optionally mono-, di- or trisubstituted by identical or different substituents, or represents a heterocyclic radical of the formula

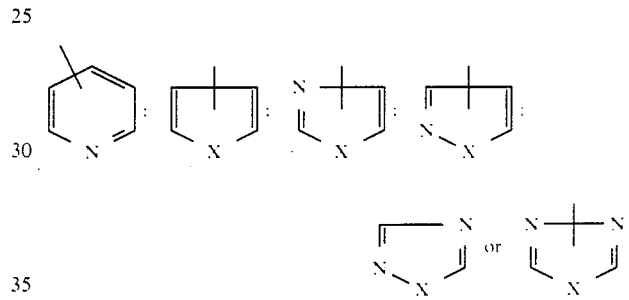

which is optionally mono-, di- or trisubstituted by identical or different substituents and/or benzo-fused, X in each case representing oxygen, sulphur or an NH group or NCH$_3$ group said substituents in each case being fluorine, chlorine, bromine, iodine, cyano, nitro, hydroxyl, methyl, ethyl, n- or i-propyl, n-, i-, s- or t-butyl, methoxy, ethoxy, n- or i-propoxy, methylthio, ethylthio, acetyl, propionyl, methylsulphinyl, methylsulphonyl, trifluoromethyl, trifluoromethoxy, trifluoromethylthio, trifluoromethylsulphinyl, trifluoromethylsulphonyl, chloroacetyl, dichloroacetyl, trifluoroacetyl, chloroethoxycarbonyl, phenyl, phenoxy, phenylthio, benzoyl, hydroxycarbonyl, methoxycarbonyl, ethoxycarbonyl, n- or i-propoxycarbonyl, allyloxycarbonyl, methoxymethoxycarbonyl, ethoxyethoxycarbonyl, hydroximinomethyl, methoxyiminomethyl, methoximinoethyl and ethoxyiminoethyl.

3. A triazolo-pyrimidine-2-sulphonamide according to claim 1, in which

R$^1$ represents methoxymethyl, and at the same time R$^2$ represents methyl, or R$^2$ represents methoxymethyl, and at the same time R$^1$ represents methyl, R$^3$ represents hydrogen and R$^4$ represents phenyl, α-naphthyl or β-naphythyl, in each case optionally mono-, di- or trisubstituted by identical or different substituents, or represents a heterocyclic radical of the formula

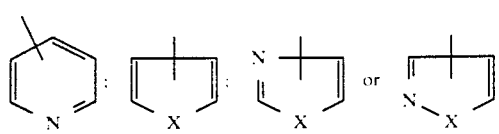

which is optionally mono-, di- or trisubstituted by identical or different substituents and/or benzo-fused, X in each case representing oxygen, sulphur or an NH group or NCH₃ group said substituents in each case being fluorine, chlorine, bromine, iodine, cyano, nitro, hydroxyl, methyl, ethyl, methoxy, methylthio, acetyl, chloroethoxycarbonyl, trifluoromethyl, trifluoromethoxy, trifluoromethylthio, phenyl, phenoxy, phenylthio hydroxycarbonyl, methoxycarbonyl, ethoxycarbonyl, allyloxycarbonyl, ethoxyethoxycarbonyl, hydroximinomethyl, methoximinomethyl and methoxyiminoethyl.

4. A triazolo-pyrimidine-2-sulphonamide according to claim 1, in which

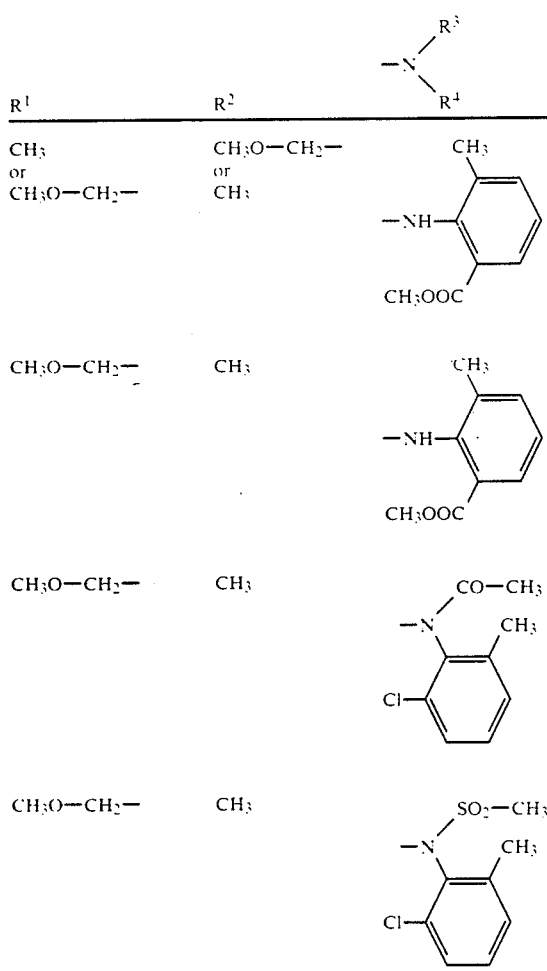

5. A triazolo-pyrimidine-2-sulphonamide according to claim 1, wherein such compound is 5-methyl-7-methoxymethyl-N-(2-chloro-6-methyl-phenyl)-1,2,4-triazolo-[1,5-a]pyrimidine-2-sulphonamide of the formula

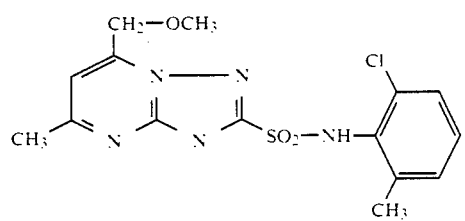

6. A triazolo-pyrimidine-2-sulphonamide according to claim 1, wherein such compound is 5-methyl-7-methoxymethyl-N-(2-bromo-phenyl-1,2,4-triazolo-[1,5-a]pyrimidine-2-sulphonamide of the formula

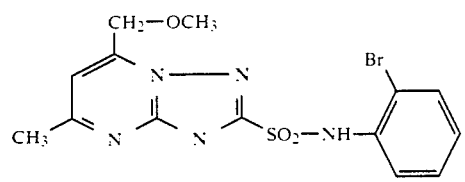

7. A method of combating unwanted vegetation which comprises applying to such vegetation or to a locus from which it is desired to exclude such vegetation a herbicidally effective amount of a triazolo-pyrimidine-2-sulphonamide according to claim 1.

8. A method according to claim 7, wherein such compound is 5-methyl-7-methoxymethyl-N-(2-chloro-6-methyl-phenyl)-1,2,4-triazolo-[1,5-a]pyrimidine-2-sulphonamide.

9. A method according to claim 7, wherein such compound is 5-methyl-7-methoxymethyl-N-(2-bromo-phenyl)-1,2,4-triazolo-[1,5-a]pyrimidine-2-sulphonamide.

10. A herbicidal composition comprising a herbicidally effective amount of a triazolo-pyrimidine-2-sulphonamide according to claim 1 and a suitable extender.

* * * * *